US010736655B1

(12) United States Patent
Pruter et al.

(10) Patent No.: US 10,736,655 B1
(45) Date of Patent: Aug. 11, 2020

(54) METHOD AND SYSTEM FOR REDUCTION OF CONTAMINATION IN NEEDLE GUIDES

(76) Inventors: Rick L. Pruter, Coralville, IA (US); Betty Sedlacek, Iowa City, IA (US)

( * ) Notice: Subject to any disclaimer, the term of this patent is extended or adjusted under 35 U.S.C. 154(b) by 1416 days.

(21) Appl. No.: 13/446,788

(22) Filed: Apr. 13, 2012

Related U.S. Application Data

(60) Provisional application No. 61/476,069, filed on Apr. 15, 2011.

(51) Int. Cl.
| | |
|---|---|
| *A61B 17/34* | (2006.01) |
| *A61B 1/00* | (2006.01) |
| *A61B 46/10* | (2016.01) |
| *A61M 25/06* | (2006.01) |

(52) U.S. Cl.
CPC ...... *A61B 17/3403* (2013.01); *A61B 1/00135* (2013.01); *A61B 46/10* (2016.02); *A61B 1/00142* (2013.01); *A61B 2017/3419* (2013.01); *A61M 25/0631* (2013.01)

(58) Field of Classification Search
CPC ...... A61M 25/0637; A61M 2005/3217; A61M 5/3216; A61M 25/007; A61M 25/0084; A61M 25/0136; A61M 2025/0087; A61M 25/0147; A61M 5/178; A61M 25/00; A61M 5/3243; B29C 45/00; G01K 1/083; A61B 1/00073; A61B 19/081; A61B 19/08; A61B 2019/084; A61B 19/10
USPC ............... 600/133, 123, 153, 156, 127, 104
See application file for complete search history.

(56) References Cited

U.S. PATENT DOCUMENTS

| | | | | | |
|---|---|---|---|---|---|
| 4,693,257 | A | * | 9/1987 | Markham | A61B 10/0283 600/565 |
| 4,757,381 | A | * | 7/1988 | Cooper | A61B 1/00091 206/369 |
| 4,877,033 | A | * | 10/1989 | Seitz, Jr. | 600/441 |
| 5,332,092 | A | * | 7/1994 | Fischer | A61M 5/002 206/305 |
| 5,433,221 | A | * | 7/1995 | Adair | A61B 46/10 128/849 |
| 7,762,949 | B2 | * | 7/2010 | Nakao | A61B 1/00073 600/104 |
| 8,905,921 | B2 | * | 12/2014 | Titus | 600/175 |
| 2005/0261674 | A1 | * | 11/2005 | Nobis | A61B 1/00073 606/45 |
| 2006/0116603 | A1 | * | 6/2006 | Shibazaki | A61B 10/0096 600/562 |
| 2007/0038181 | A1 | * | 2/2007 | Melamud et al. | 604/158 |
| 2010/0198013 | A1 | * | 8/2010 | Binmoeller | 600/121 |
| 2012/0232342 | A1 | * | 9/2012 | Reydel | 600/104 |

* cited by examiner

*Primary Examiner* — Angela M Hoffa
*Assistant Examiner* — Helene Bor
(74) *Attorney, Agent, or Firm* — Simmons Perrine Moyer Bergman PLC

(57) ABSTRACT

A system and method for reducing the risk of contamination of interior regions of a needle guide which is disposed on an endocavity transducer, which system includes an elastic membrane forming a pocket which covers a needle exit hole in the needle guide. The pocket is disposed on a sheath which is both; disposed around the endocavity transducer and between the endocavity transducer and the needle guide.

5 Claims, 2 Drawing Sheets

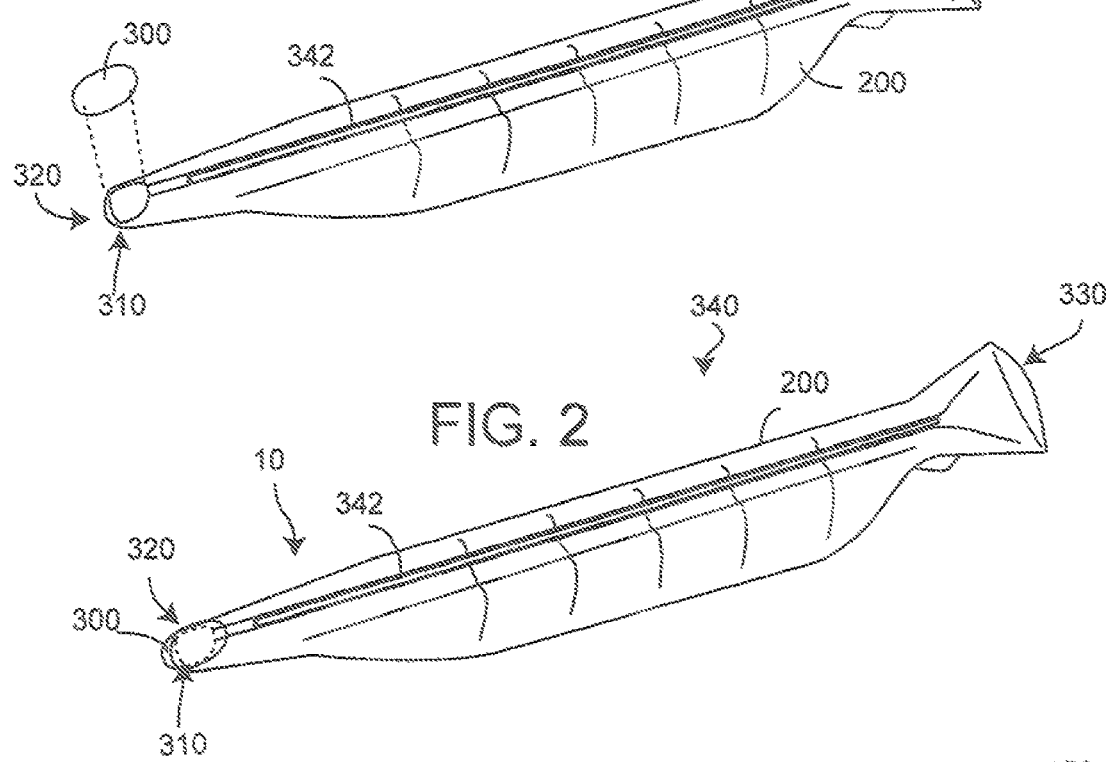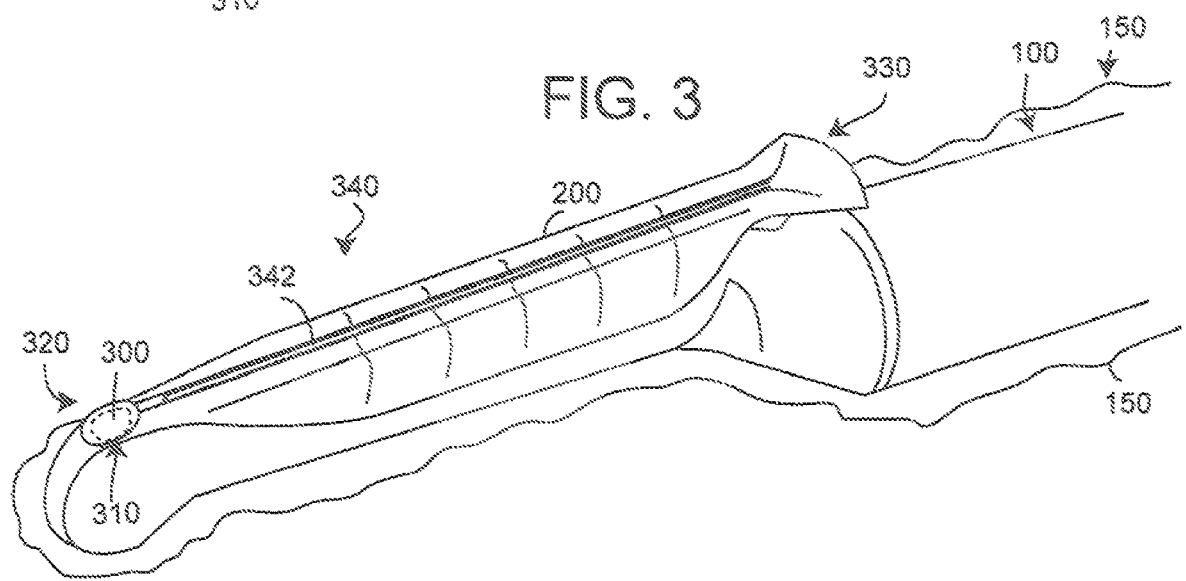

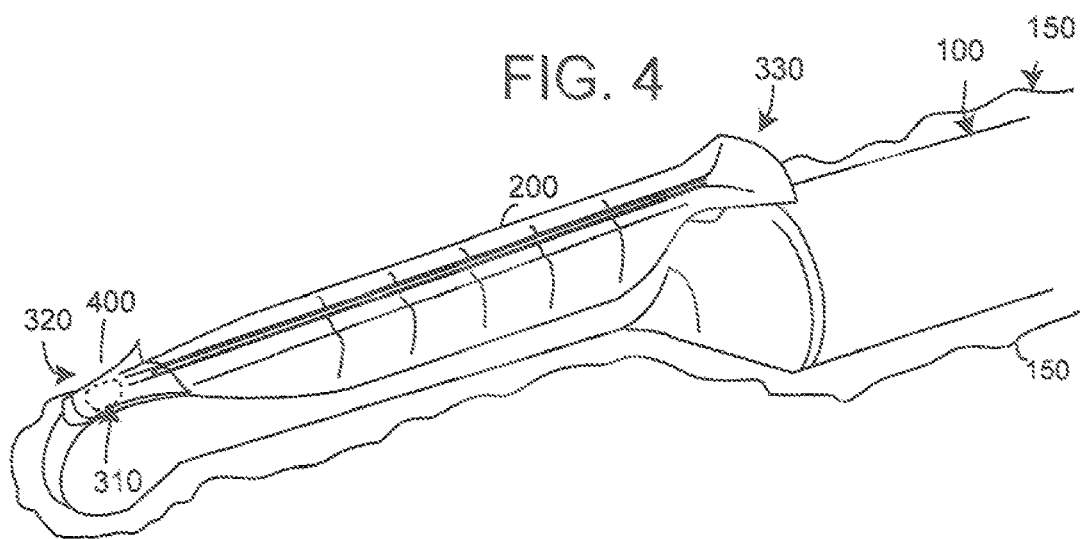
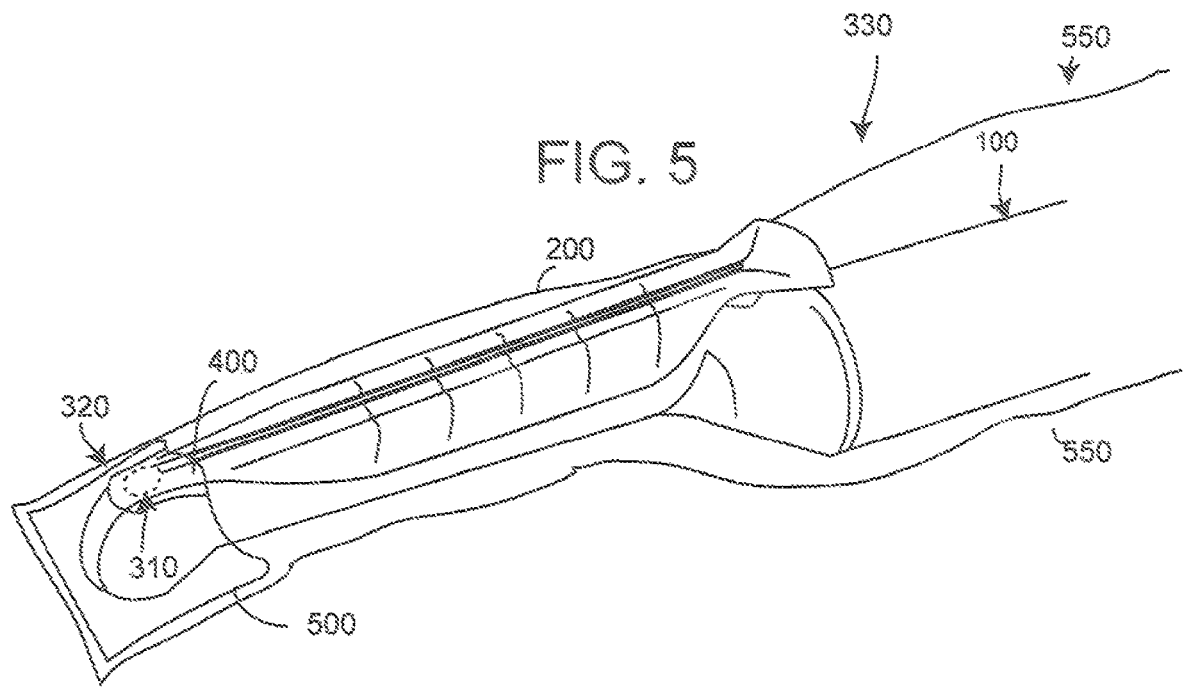

METHOD AND SYSTEM FOR REDUCTION OF CONTAMINATION IN NEEDLE GUIDES

FIELD OF THE INVENTION

The present invention generally relates to medical equipment, and more particularly relates to medical equipment which must be covered with a sheath during medical procedures, and even more particularly relates to methods and systems for reducing contamination of interior spaces of a needle/cannula guide when disposed outside of a sheath around an endocavity transducer.

BACKGROUND OF THE INVENTION

In recent years, medical professionals have used various types of biopsy systems to collect tissue from internal regions of the body. These biopsy systems are typically either enclosed in a sterile disposable sheath prior to use on any patient, or they are cleaned after use. The biopsy system or transceiver may be a mechanical or electro-mechanical device. Often a sheath is place over the biopsy system and then a needle/cannula guide is coupled to the biopsy system but on the outside of the sheath. In such configurations, the needle guide is not protected by the sheath.

When the sheath covered system with an externally mounted needle guide is inserted into a rectal or vaginal cavity or surgical incision, contaminants may enter and contaminate internal sections of the needle guide. It is well known to use a second sheath to cover the entire combination including the previously externally mounted needle guide.

While such double sheath procedures have been used extensively in the past, the doubling of these sheaths doubles the sheath cost and is more time consuming and, therefore, even more costly.

Consequently, there exists a need for improved methods and systems for protecting internal sections of needle guides mounted to sheath covered biopsy systems in an efficient manner, while simultaneously maintaining the sterile or aseptic state of the internal spaces in the needle guide when portions of the entire combination are inserted into a body cavity.

SUMMARY OF THE INVENTION

It is an object of the present invention to provide a system and method for covering portions of needle guides which are mounted to sheath covered biopsy systems in an efficient manner.

It is a feature of the present invention to utilize a sterile hole cover which is configured to cover an otherwise exposed needle or cannula exit hole in an externally mounted needle guide.

It is another feature of the present invention to include a relatively small adhesive needle hole cover.

It is an advantage of the present invention to provide reduced ability for contamination to enter inside a needle guide when it is inserted into a body cavity.

It is another advantage of the present invention to reduce cost for protecting needle guides which are not covered by a sheath.

The present invention is an apparatus and method for covering exit needle holes for needle guides for use with biopsy systems designed to satisfy the aforementioned needs, provide the previously stated objects, include the above-listed features, and achieve the already articulated advantages. The present invention is carried out in a "wasted time-less" manner in a sense that the time consumed, in adding a second full sheath over the needle guide, has been eliminated. The invention is also accomplished in a "tear-less" or "contamination-less" manner in the sense that the contamination that may be exposed to the internal areas of the needle guide through a tear in a outer sheath of a double sheath arrangement, after a needle is caused to exit the inside of the outer sheath, has been reduced.

Accordingly, the present invention is a system and method including a self-sealing needle or cannula exit hole cover for use on a needle guide mounted outside of any sheath.

BRIEF DESCRIPTION OF THE DRAWINGS

The invention may be more fully understood by reading the following description of the preferred embodiments of the invention, in conjunction with the appended drawings wherein:

FIG. 1 is an exploded perspective view of the contamination reducing system of the present invention, which shows a needle guide with a detached exit hole cover.

FIG. 2 is a perspective view of the contamination reducing system of FIG. 1, which shows a needle guide with an attached exit hole cover, where the dotted line shows the now covered exit hole.

FIG. 3 is a perspective view of the present invention attached to a sheath covered biopsy system.

FIG. 4 is a perspective view of the contamination reducing system of the present invention, which shows a needle guide with attached terminal boot, where the dotted line shows the now covered exit hole.

FIG. 5 is a perspective view of the contamination reducing system of the present invention with a terminal boot which is integrated into a pocket at the end of a sheath, where the dotted line shows the now covered exit hole.

DETAILED DESCRIPTION

Now referring to the drawings wherein like numerals refer to like matter throughout, and more specifically referring to FIGS. 1 and 2, there is shown a needle guide system of the present invention generally designated 10, which includes a needle or biopsy cannula guide 200, of the prior art, which can be similar to many different prior art needle guides especially those having an elongated central section 340 which is configured to have a rear or proximal portion 330 thereof remain outside of the body when the front or distal portion 320 is inserted into the body orifice near the tissue to be penetrated by the needle or biopsy cannula. The guide 200 is attached to the ultrasound transducer 100, but only after the ultrasound transducer is covered with a sheath 150.

The present invention is a method and system for protecting the inside of the needle guide from contamination without the use of a complete second sheath.

Instead, a relatively small membrane 300 is disposed over a needle or cannula exiting hole 310 (shown with dashed lines in FIG. 2) on the front end 320 of the needle guide 200, this membrane 300 covers the exit hole 310 of the needle guide 200 so that when it is inserted into a patient there is no contamination entering the inside of the needle guide 200 via the exit hole 310. When the transducer 100, with associated sheath 150 and attached needle guide 200 is inserted into the rectal or vaginal cavity, a needle is then pressed through the membrane 300 into the patient's tissue. The needle pierces the membrane 300 but, in one embodiment, the membrane 300 while remaining attached to the needle guide 200, also clings to the needle or biopsy cannula so as to reduce contamination from entering the inside of the needle guide 200.

The membrane 300 can be a small piece of material similar to that used for sheaths or other suitable materials. The membrane 300 may be held in place by an adhesive which bonds with the outside of the needle guide 200. The membrane can also be welded to the needle guide 200. Ideally the membrane 300 is an elastic material, but any material could be used. For example, regular transparent tape placed over the needle exit hole 310 of a needle guide 200 could be a very crude example of a membrane 300. When the needle or cannula 400 is removed from the patient and retracted into the needle guide 200, the membrane 300 may cling to the needle and reduce contaminants from being drawn into the needle guide 200 on the exterior of the needle.

The membrane 300 however, in one embodiment, will specifically exclude any type of cover which covers any substantial portion of the transducer 100 so as to provide substantial shielding (either primary or secondary redundant shielding) of the transducer 100 from contaminants. Additionally, the membrane 300, in one embodiment, shall not include any material which covers substantially all of the needle guide 200. In another embodiment, the membrane 300 might cover the entire needle guide 200.

The membrane 300 can also be used to detect whether the guide 200 has been previously used, in such cases the membrane will be broken.

In one embodiment, the membrane 300 can be used on numerous different types of needle guides. In another embodiment the membrane 300 may be custom fit for a particular needle guide.

The membrane 300 in one embodiment could be attached by the physician or other medical imaging professional before the insertion of the needle guide 200 into the patient. In another embodiment, the membrane 300 could be attached to the needle guide 200 by the manufacturer or other assembly, inspection or certification personnel.

Now referring to FIG. 4, there is shown an embodiment of the present invention which utilizes a boot 400, instead of the membrane 300, of FIGS. 1-3. Boot 400 may extend over the exit hole 310 and also extend around the entire front or distal end of needle guide 200. The material and method of attachment of boot 400 can be similar to membrane 300. In FIG. 4 the boot 400 is a separate from the sheath 150 and may be attached to the needle guide 200 by the physician or by the manufacturer or other personnel.

Now referring to FIG. 5, there is shown a system of the present invention where the boot 400 of FIG. 4, is incorporated into an exterior pocket 500, which is located on sheath 550. Sheath 550 may be similar to sheath 150 except for the pocket 500 and the boot 400. In an alternate embodiment the combination of the pocket 500 and the exterior of the sheath 550 adjacent to the pocket 500 may essentially form a boot which functions much like boot 400 of FIG. 4.

In operation, the apparatus and method of the present invention as described in FIGS. 1-3, could function as follows: the biopsy system 100 is covered with a sheath 150 and then a needle guide 200 is attached thereto on the exterior of the sheath 150, the combination of the biopsy system 100, sheath 150 and needle guide 200 (with membrane 300 attached thereto) is inserted into a body cavity of a patient. When the distal portion of the biopsy system 100 and the distal portion of needle guide 200 are inside the body cavity the needle is inserted into the proximal end 330 of needle guide 200 and passes through an intermediate channel or cannula 342 and then the needle is manipulated from the proximal end 330 of the needle guide 200. Tissue may be removed from the patient via the needle/cannula and retracted from the needle guide 200 which is also removed from the patient. The boot 400 would function very similarly to the system with membrane 300.

The pocket 500 would work very similar except that the distal end of the needle guide would be covered by the boot 400 or pocket 500 by inserting the distal end of the needle guide into the boot 400 or pocket 500 which is already attached to sheath 550 which has already been disposed over the biopsy system 100.

Throughout this description, reference is made to sterile or a sterile sheath or other sterile items. It should be understood that this could refer to any state of cleanliness with respect to living organisms or a media upon which living organisms could grow. The present invention is intended to cover items that are aseptic, as well as sterile.

Throughout this description, reference is made to a physician. The present invention is intended to apply to any person, such as, but not limited to, physicians, physicians' assistants, nurses, medical imaging specialists, veterinarians, veterinarians' assistants, industrial clean room technicians, etc.

Throughout this description, reference is made to a biopsy system or other medical equipment. The present invention may be applicable to any environment, such as, but not limited to, medical, veterinary or clean room applications, etc.

Throughout this description the term needle is used to refer to an elongate object that enters a patients tissue, it should be understood that this term is intended to refer to cannulas as well as needles. Similarly the term needle guide as used herein is intended to refer to cannula guides, which are capable of guiding cannulas.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

We claim:

1. A system for protecting inside surfaces of a needle guide, from contamination entering through a needle exit hole of the needle guide, the system comprising:
   an endoscope imaging device having a distal endoscope end configured to be inserted inside a body cavity of a human, a proximal endoscope end configured to remain outside the body;
   a needle guide configured to be directly disposed on, supported by and directly coupled to and partially enshroud an exterior surface of said endoscope imaging device, said needle guide having a distal end and a proximal end and a needle exit hole therein distal of said proximal end, said needle exit hole having a needle exit hole radius, which has a needle exit hole perimeter dimension; an intermediate linear channel is disposed between the needle exit hole and the proximal end; said intermediate linear channel is sized and configured so the said proximal end remains outside the body;
   said distal end disposed in proximity to said distal endoscope end;

said needle exit hole and said intermediate linear channel are configured to allow a needle or cannula which is inserted into the proximal end of the needle guide to exit the needle guide; and a disposable piece of adhesive tape, with a disposable piece of adhesive tape perimeter dimension which is larger than said needle exit hole perimeter dimension, said disposable piece of adhesive tape only contact an engagement zone, having an engagement zone outer perimeter dimension, which is larger than said needle exit hole perimeter dimension, said engagement zone located only on an external needle guide surface of said needle guide and only around a periphery of said needle exit hole, where said disposable piece of adhesive tape extends completely over said engagement zone and completely covers said needle exit hole and said disposable piece of adhesive tape is not configured to contact a portion of an endoscope imaging device;

wherein said piece of adhesive tape contacts only an in-substantial amount of the external surface area of said needle guide: and wherein a layered configuration exists beginning with said exterior portion of said endoscope imaging device; a portion of the needle guide, and the disposable piece of adhesive tape.

2. A system for protecting inside surfaces of a needle guide, which is coupled to an endoscope imaging device, from contamination entering through a needle exit hole of the needle guide, the system comprising:

a needle guide configured to be directly disposed on, supported by and directly coupled to and partially enshroud an exterior surface of an endoscope imaging device, having a distal endoscope end configured to be inserted inside a body cavity of a human and a proximal endoscope end configured to remain outside the body, said needle guide having a distal end and a proximal handle end and a needle exit hole therein distal of said proximal handle end, said needle exit hole is configured to allow a needle or cannula which is inserted into the needle guide to exit the needle guide;

said distal end disposed in proximity to said distal endoscope end; and a disposable piece of adhesive tape securely attached to an external needle guide surface of said needle guide around a periphery of said needle exit hole, where said disposable piece of adhesive tape extends completely over and completely covers said needle exit hole and said disposable piece of adhesive tape is not configured to contact a portion of an endoscope imaging device; and said disposable piece of adhesive tape securely attached to an engagement zone, having an engagement zone radial dimension, which is larger than said needle exit hole radial dimension, of an external needle guide surface of said needle guide around a periphery of said needle exit hole.

3. A system for protecting inside surfaces of a needle guide, which is directly coupled to an endoscope imaging device, from contamination entering through a needle exit hole of the needle guide, the system comprising:

a needle guide directly disposed on, supported by, directly coupled to and partially enshroud an exterior surface of an endoscope imaging device, having a distal endoscope end configured to be inserted inside a body cavity of a human and a proximal endoscope end configured to remain outside the body;

said needle guide having a distal end and a proximal handle end and a needle exit hole therein distal of said proximal handle end, said needle exit hole is configured to allow a needle or cannula which is inserted into the needle guide to exit the needle guide;

said distal end disposed in proximity to said distal endoscope end;

a disposable piece of adhesive tape securely attached to an external needle guide surface of said needle guide around a periphery of said needle exit hole, where said disposable piece of adhesive tape extends completely over and completely covers said needle exit hole and said disposable piece of adhesive tape is not configured to contact a portion of an endoscope imaging device; said disposable piece of adhesive tape securely attached to an engagement zone, having an engagement zone radial dimension, which is larger than said needle exit hole radial dimension, of an external needle guide surface of said needle guide around a periphery of said needle exit hole;

a disposable sheath configured to be disposed about an endoscope imaging device;

said piece of adhesive tape is coupled to an exterior portion of said disposable sheath; and wherein a configuration exists beginning with a portion of the disposable sheath, which is covered by the needle guide, and finally the disposable piece of adhesive tape covering only a portion of the needle guide.

4. A method of protecting an inside of a needle guide comprising the steps of:

providing an endoscope imaging device having a distal endoscope end configured to be inserted inside a body cavity of a human and a proximal endoscope end configured to remain outside the body;

providing a disposable sheath disposed about said endoscope imaging device;

providing a needle guide configured to be disposed on said disposable sheath, supported by and indirectly coupled, through said disposable sheath, to and partially enshroud an exterior surface of an endoscope imaging device, said needle guide having a distal end and a proximal handle end and a needle exit hole therein distal of said proximal handle end, said needle exit hole is configured to allow a needle or cannula which is inserted into the needle guide to exit the needle guide while inside a body cavity;

said distal end disposed in proximity to said distal endoscope end;

providing a disposable piece of adhesive tape securely attached to an external needle guide surface of said needle guide around a periphery of said needle exit hole, where said piece of adhesive tape extends radially beyond and completely covers said needle exit hole and does not contact a portion of said endoscope imaging device; said disposable piece of adhesive tape securely attached to an engagement zone, having an engagement zone radial dimension, which is larger than said needle exit hole radial dimension, of an external needle guide surface of said needle guide around a periphery of said needle exit hole;

providing an adhesive, disposed between and coupling said needle guide and said piece of adhesive tape;

wherein a layered configuration exists beginning with the exterior surface of said endoscope imaging device, said disposable sheath, then the needle guide, then finally the disposable piece of adhesive tape.

5. A method of protecting an inside of a needle guide comprising the steps of:

providing an endoscope imaging device having a distal endoscope end configured to be inserted inside a body cavity of a human and a proximal endoscope end configured to remain outside the body;

providing a disposable sheath disposed about said endoscope imaging device;

providing a needle guide configured to be directly disposed on, supported by and directly coupled to and partially enshroud an exterior surface of an endoscope imaging device, said needle guide having a distal end and a proximal handle end and a needle exit hole therein distal of said proximal handle end, said needle exit hole is configured to allow a needle or cannula which is inserted into the needle guide to exit the needle guide while inside a body cavity; said distal end disposed in proximity to said distal endoscope end;

providing a disposable piece of adhesive tape securely attached to an external needle guide surface of said needle guide around a periphery of said needle exit hole, where said piece of adhesive tape extends radially beyond and completely covers said needle exit hole and does not contact a portion of said endoscope imaging device; and said disposable piece of adhesive tape securely attached to an engagement zone, having an engagement zone radial dimension, which is larger than said needle exit hole radial dimension, of an external needle guide surface of said needle guide around a periphery of said needle exit hole;

providing an adhesive, disposed between and coupling said needle guide and said piece of adhesive tape;

wherein said piece of adhesive tape is coupled to an exterior portion of said sheath and a layered configuration exists beginning with the exterior surface of said endoscope imaging device, said disposable sheath, then the needle guide, then the adhesive and finally the disposable piece of adhesive tape.

* * * * *